United States Patent

Ray et al.

[11] Patent Number: 4,885,294
[45] Date of Patent: Dec. 5, 1989

[54] 2-ARYL-3-(SUBSTITUTED PIPERAZINYL)-1-(1H-1,2,4-TRIAZOLYL)-PROPANOL-2-OL ANTIFUNGAL AGENTS

[75] Inventors: Stephen J. Ray, Deal; Kenneth Richardson, Birchington, both of England

[73] Assignee: Pfizer Inc., New York, N.Y.

[21] Appl. No.: 268,821

[22] Filed: Nov. 8, 1988

[30] Foreign Application Priority Data

Dec. 12, 1987 [GB] United Kingdom ............... 8729083

[51] Int. Cl.⁴ ................. A01N 43/60; C07D 401/14; C07D 413/14; C07D 417/14
[52] U.S. Cl. ..................... 514/227.8; 514/252; 514/253; 514/228.2; 514/233.8; 514/235.2; 514/236.2; 544/366; 544/121; 544/58.6; 544/363; 544/368; 544/364
[58] Field of Search ............... 514/252, 253, 227.8, 514/228.2, 233.8, 235.2, 236.2; 544/366, 121, 58.6, 363, 368, 364

[56] References Cited

U.S. PATENT DOCUMENTS 4,738,962 4/1988 Holmwood et al. ............... 514/252

FOREIGN PATENT DOCUMENTS 0180850 5/1986 European Pat. Off.

OTHER PUBLICATIONS

Holmwood et al., Chemical Abstracts, vol. 105, entry 220995e (1986).

Primary Examiner—John M. Ford
Attorney, Agent, or Firm—Peter C. Richardson; J. Trevor Lumb; James M. McManus

[57] ABSTRACT

An antifungal agent of the formula:

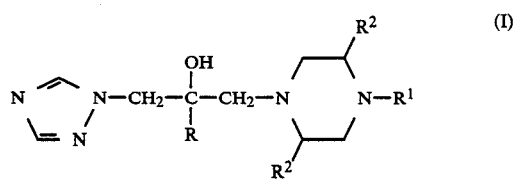

wherein
R is phenyl group which may be substituted by 1 to 3 substituents each independently selected from halo and $CF_3$; $R^1$ is either (a) a phenyl group substituted by a group of the formula $—N=CH—N(C_1-C_4 \text{ alkyl})_2$,

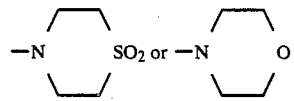

or (b) a 5- or 6-membered aromatic heterocyclic group which may be benzo-fused and substituted by 1 or 2 substituents each independently selected from halo, $C_1-C_4$ alkyl and halo-($C_1$ or $C_2$ alkyl), said heterocyclic group being attached to the nitrogen atom of the piperazine ring by a carbon atom; and
$R^2$ is H or $CH_3$; or an O-ester or O-ether thereof which is a $C_2-C_4$ alkanoyl or benzoyl ester, or a $C_1-C_4$ alkyl, $C_2-C_4$ alkenyl, phenyl-($C_1-C_4$ alkyl) or phenyl ether, said phenyl and benzoyl groups of said O-esters and O-ethers may be substituted by one or two substituents each selected from $C_1-C_4$ alkyl, halo and halo-($C_1$ or $C_2$ alkyl); or a pharmaceutically acceptable salt thereof.

12 Claims, No Drawings

2-ARYL-3-(SUBSTITUTED PIPERAZINYL)-1-(1H-1,2,4-TRIAZOLYL)-PROPANOL-2-OL ANTIFUNGAL AGENTS

This invention relates to novel triazole derivatives which have antifungal activity and are useful in the treatment of fungal infections in animals, including humans, and as agricultural fungicides.

According to the invention, there are provided compounds of the formula:

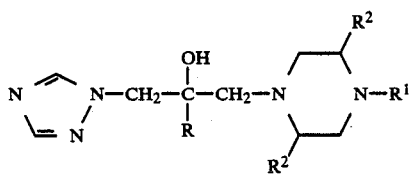

where
R is a phenyl group which may be substituted by 1 to 3 substituents each independently selected from halo and $CF_3$; $R^1$ is either (a) a phenyl group substituted by a group of the formula $-N=CH-N(C_1-C_4 \text{ alkyl})_2$,

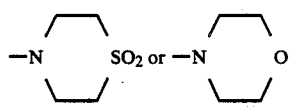

or (b) a 5- or 6-membered aromatic heterocyclic group which may be benzo-fused and substituted by 1 or 2 substituents each independently selected from halo, $C_1-C_4$ alkyl and halo-($C_1$ or $C_2$ alkyl), said heterocyclic group being attached to the nitrogen atom of the piperazine ring by a carbon atom;
and
$R^2$ is H or $CH_3$;
and
the O-esters and O-ethers thereof (as hereinafter defined);
and the pharmaceutically and agriculturally acceptable salts of said compounds and esters and ethers.

"Halo" means F, Cl, Br or I. The preferred alkyl groups are methyl and ethyl. The preferred haloalkyl groups are mono- and di-chloro-($C_1-C_2$ alkyl) and $CF_3$.

Preferably, R is a phenyl group optionally substituted by 1 or 2 substituents each selected from halo (preferably F or Cl) and $CF_3$. Specific examples of R include 4-fluorophenyl, 4-chlorophenyl, 4-bromophenyl, 4-iodophenyl, 4-trifluoromethylphenyl, 2-chlorophenyl, 2,4-dichlorophenyl, 2,4-difluorophenyl, 2-chloro-4-fluorophenyl, 2-fluoro-4-chlorophenyl, 2,5-difluorophenyl, 2,4,6-trifluorophenyl and 4-bromo-2,5-difluorophenyl.

Most preferably, R is 2,4-dichlorophenyl or 2,4-difluorophenyl.

Examples of said 5- or 6-membered aromatic heterocyclic group are pyridyl, pyrazinyl, pyrimidinyl, pyridazinyl, thiazolyl, thiadiazolyl, isothiazolyl, oxazolyl, oxadiazolyl, isoxazolyl, triazolyl, tetrazolyl, quinolyl, isoquinolyl, benzothiazolyl and benzoxazolyl, all optionally substituted by 1 or 2 substituents each selected from halo, $C_1-C_4$ alkyl and halo-($C_1$ or $C_2$ alkyl).

Preferably, said aromatic heterocyclic group is a 2-, 3- or 4-pyridyl, 2-, 3- or 4-quinolyl, 2-benzothiazolyl or 2-benzoxazolyl group, optionally substituted as defined above.

More preferably, said aromatic heterocyclic group is an unsubstituted 2-pyridyl, 2-quinolyl, 2-benzothiazolyl or 2-benzoxazolyl group.

When $R^1$ is a substituted phenyl group as defined in part (a) of formula (I), said substituent is preferably in the 4-position.

$R^1$ is most preferably a group of the formula:

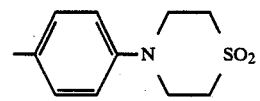

$R^2$ is preferably H. When each $R^2$ is $CH_3$, the compounds are preferably in the cis-form.

The O-esters are $C_2-C_4$ alkanoyl (e.g. acetyl) and benzoyl esters. The phenyl ring of benzoyl esters can be substituted by 1 or 2 substituents each selected from $C_1-C_4$ alkyl, halo and halo-($C_1$ or $C_2$ alkyl). The O-ethers are $C_1-C_4$ alkyl, $C_2-C_4$ alkenyl, phenyl-($C_1-C_4$ alkyl) and phenyl ethers. Again said phenyl groups can be ring substituted by 1 or 2 substituents selected from $C_1-C_4$ alkyl, halo and halo-($C_1$ or $C_2$ alkyl).

The invention also provides a pharmaceutical composition comprising a compound of the formula (I) or an O-ester, O-ether or pharmaceutically acceptable salt thereof, together with a pharmaceutically acceptable diluent or carrier.

The invention further provides a compound of the formula (I) or an O-ester, O-ether or pharmaceutically acceptable salt thereof, for use as a medicament.

The invention yet further provides an antifungal composition for agricultural (including horticultural) use, comprising a compound of the formula (I) or an O-ester, O-ether or agriculturally acceptable salt thereof, together with an agriculturally acceptable diluent or carrier.

The invention yet further provides a method of treating an animal (including a human being), plant or seed having a fungal infection, which comprises treating said animal, plant or seed, or the locus of said plant or seed, with an effective amount of a compound of the formula (I) or O-ester or O-ether thereof or with, as appropriate, a pharmaceutically or agriculturally acceptable salt thereof.

The compounds of the formula (I), except for those in which $R^1$ is phenyl substituted by $-N=CH-N(C_1-C_4$ alkyl$)_2$, can be prepared by the following reaction scheme:

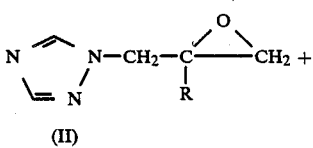

(II)

-continued

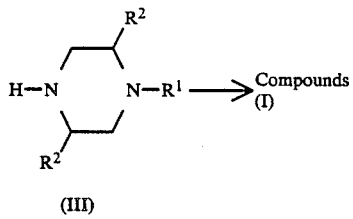

The reaction is typically carried out in a suitable organic solvent, e.g. dioxan or dimethylformamide, at up to the reflux temperature of the reaction mixture. It is also possible to use the oxirane (II) in acid addition salt form, e.g. as the methanesulphonate, provided a neutralizing amount of a base such as potassium carbonate is present. The product of the formula (I) can be isolated and purified conventionally.

The starting materials of the formula (II) are known (see e.g. EP-A-44605 and EP-A-69442). The starting materials of the formula (III) are either known compounds or can be prepared conventionally, e.g. as described in the following Preparations section.

The compounds of the formula (I) in which $R^1$ is a phenyl group substituted by a group of the formula

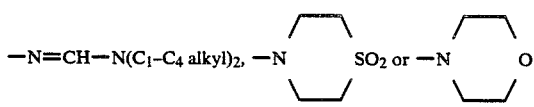

can be prepared from the following intermediates:

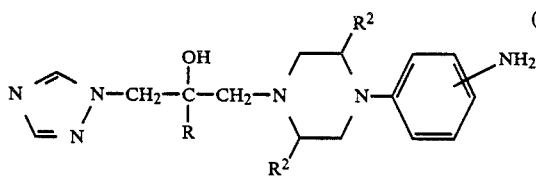

The —$NH_2$ group is preferably in the 4-position of the benzene ring.

These novel intermediates also form a part of this invention.

To prepare compounds in which $R^1$ is phenyl substituted by

compound (IV) is reacted with divinylsulphone. The reaction is carried out in a suitable organic solvent, e.g. ethanol, at up to the reflux temperature. The product can then be isolated conventionally.

To prepare compounds in which $R^1$ is phenyl substituted by

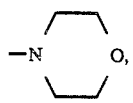

compound (IV) is reacted with a compound of the formula $X—(CH_2)_2—O—(CH_2)_2—X^1$ where X and $X^1$ are leaving groups, e.g. chloro, bromo or methanesulphonyloxy. X and $X^1$ are preferably Cl. The reaction is typically carried out at up to the reflux temperature in a suitable organic solvent, e.g. ethanol, dioxan, tetrahydrofuran or dimethylformamide, and preferably in the presence of an acid acceptor such as potassium carbonate. The product can again be isolated and purified by conventional methods.

To prepare compounds in which $R^1$ is phenyl substituted by —N=CH—N($C_1$-$C_4$ alkyl)$_2$, the compound (IV) is reacted with a dimethyl or diethyl acetal of the formula ($C_1$-$C_4$ alkyl)$_2$NCH($C_1$-$C_2$ alkoxy)$_2$. The reaction is carried out in a suitable organic solvent, e.g. ethanol, at up to the reflux temperature, following which the product can again be isolated and purified conventionally.

The starting materials of the formula (IV) can be prepared by the technique described in the following Preparations section.

The O-esters and O-ethers can be prepared conventionally, typically by reacting an alkali metal salt of a compound of the formula (I) with the appropriate chloro- or bromo-compound, e.g. an alkanoyl or benzoyl chloride, or alkyl, alkenyl, benzyl or phenyl chloride or bromide.

Where the compounds contain one or more optically active centres, then the invention includes both the resolved and unresolved forms, including diastereomers.

Pharmaceutically acceptable acid addition salts of the compounds of the formula (I) are those formed from strong acids which form non-toxic acid addition salts, such as hydrochloric, hydrobromic, sulphuric and methanesulphonic acids. Such salts are also useful for agricultural use.

The salts may be obtained by conventional procedures, e.g. by mixing solutions containing approximately equimolar amounts of the free base and desired acid, and the required salt is collected by filtration, if insoluble, or by evaporation of the solvent.

The compounds of the formula (I) and their O-esters, O-ethers and salts are antifungal agents, useful in combating fungal infections in animals, including humans. For example they are useful in treating topical fungal infections in man caused by, among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus flavus, Aspergillus fumigatus,* Coccidioides, Paracoccidioides, Histoplasma or *Blastomyces*.

The in vitro evaluation of the antifungal activity of the compounds can be performed by determining the minimum inhibitory concentration (m.i.c.) which is the concentration of the test compounds, in a suitable medium, at which growth of the particular micro-organism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Aspergillus fumigatus,* Trichophyton spp; Microsporum spp;

*Epidermophyton floccosum, Coccidioides immitis* and *Torulopsis glabrata.*

The in vivo evaluation of the compounds can be carried out at a series of dose levels by intraperitoneal or intravenous injection or by oral administration, to mice which are inoculated with, e.g., a strain of *Candida albicans* or *Aspergillus fumigatus.* Activity is based on the survival of a treated group of mice after the death of an untreated group of mice. The dose level at which the compound provides 50% protection against the lethal effect of the infection ($PD_{50}$) is noted.

For human use, the antifungal compounds of the formula (I) and their salts, O-ethers and O-esters can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) and their salts, O-ethers and O-esters will be from 0.1 to 10 mg/kg (in divided doses) when administered by either the oral or parenteral route. Thus tablets or capsules of the compounds will contain from 5 mg to 0.5 g of active compound for administration. singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and their O-ethers, O-esters and salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions typically contain from 0.01 to 95 wt%, preferably 0.01 to 1 wt.%, of the active ingredient. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack.

For field use, likely application rates of the active ingredient are from 5 to 500 g/10 ares.

The following Examples, in which all temperatures are in °C., illustrate the invention:

EXAMPLE 1

3-[4-(Benzothiazol-2-yl)-piperazin-1-yl]-2-(2,4-dichlorophenyl)-1-(1H-1,2,4-triazol-1-yl)propan-2-ol

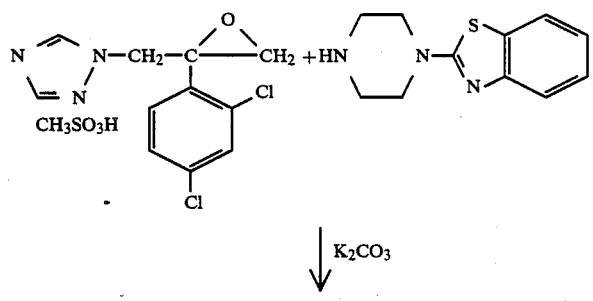

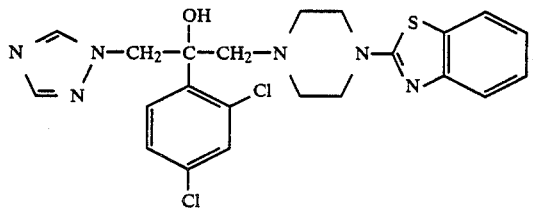

A mixture of benzothiazol-2-yl-piperazine (0.4 g, 1.55 mmole), 2-(2,4-dichlorophenyl)-2-(1H-1,2,4-triazol-1-ylmethyl)oxirane methanesulphonate (see EP-A-44605) (0.57 g, 1.55 mmole) and potassium carbonate (2 g, 14 mmole) in dioxan (20 ml) was heated at reflux for 3 days. After cooling, the mixture was diluted with methylene chloride, the insoluble inorganic material removed by filtration and the filtrate concentrated under reduced pressure. The resulting oil was purified by flash chromatography on silica gel eluting with ether (93): ethanol (7): 0.88 ammonia solution (1) to yield the desired product as a foam, m.p. 68°–85° (0.34 g, 44%).

Analysis %: Found: C, 53.55; H, 4.21; N, 16.79; Calculated for $C_{22}H_{22}Cl_2N_6OS.1/20\ CH_2Cl_2$: C, 53.65; H, 4.51; N, 17.02.

EXAMPLES 2 AND 3

The following compounds were prepared similarly to the procedure of Example 1 starting from the same oxirane and the appropriate N-substituted piperazine. In these Examples, the products were isolated as a foam from diethyl ether.

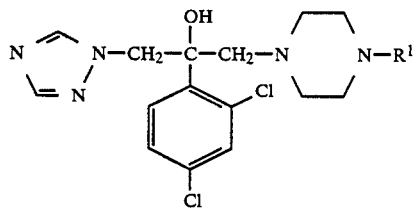

| Example No. | R¹ | Form Characterised | m.p. (°C.) | Analysis % (Found in brackets) C | H | N |
|---|---|---|---|---|---|---|
| 2 | (benzoxazolyl) | 1/6 Et₂O.⅓ H₂O | 80–100° | 59.23 (59.24 | 5.27 5.21 | 16.79 16.62) |
| 3 | (quinolinyl) | ⅓ Et₂O.⅓ H₂O | 60–80° | 55.48 (55.78 | 5.09 4.83 | 16.87 16.52) |

The preparation of 1-(benzothiazol-2-yl)piperazine is described in J. Med. Chem., 15, 693 (1972), and, of 1-(2-quinolyl)piperazine, in GB 1,107,652 and C.A., 69, P 52179j. The preparation of 1-(benzoxazol-2-yl)piperazine is described in the following Preparations section.

EXAMPLE 4

2-(2,4-dichlorophenyl)-3-{4-(4-[1,1-dioxotetrahydrothiazin-4-yl]phenyl)piperazin-1-yl}-1-(1H-1,2,4-triazol-1-yl)propan-2-ol

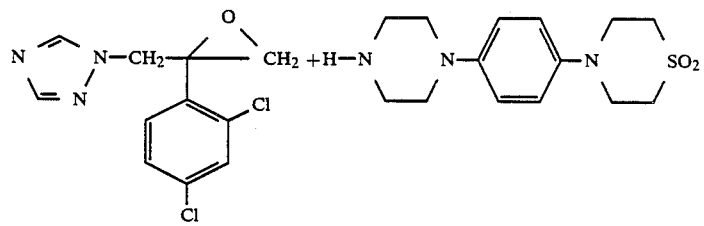

↓

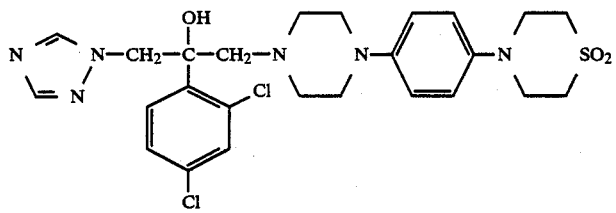

A mixture of the free base of 2-(2,4-dichlorophenyl)-2-(1H-1,2,4-triazol-1-ylmethyl)oxirane (0.3 g, 1.1 mmole), 1-(4-[1,1-dioxotetrahydrothiazin-4-yl]phenyl)piperazine (0.295 g, 1 mmole) in dioxan (15 ml) was heated under reflux for 6 days. After cooling, the solvent was removed under reduced pressure and the residue was purified by flash chromatography eluting with ethyl acetate (99): methanol (1) to yield, after collection and evaporation of appropriate fractions, the desired product as a colourless solid, m.p. 68°–70° (0.354 g, 58%).

Analysis %: Found: C, 53.17; H, 5.57; N, 13.71; Calculated for $C_{25}H_{30}Cl_2N_6O_3S.\frac{1}{2} CH_3CO_2Et$: C, 53.20; H, 5.58; N, 13.79.

EXAMPLE 5

2-(2,4-Difluorophenyl)-3-{4-(4-[1,1-dioxotetrahydrothiazin-4-yl]phenyl)piperazin-1-yl}-1-(1H-1,2,4-triazol-1-yl)propan-2-ol The title compound, m.p. 165°–7°, was prepared similarly to the procedure of Example 4 starting from the same piperazine and 2-(2,4-difluorophenyl)-2-(1H-1,2,4-triazol-1-ylmethyl)oxirane. In this Example, the eluent used in the chromatography step was ethyl acetate:methanol (98:2) and the product was recrystallized from ethyl acetate.

Analysis %: Found: C, 56.22; H, 5.63; N, 14.32; Calculated for $C_{25}H_{30}F_2N_6O_3S.\frac{1}{2} CH_3CO_2Et$: C, 56.25; H, 5.90; N, 14.58.

EXAMPLE 6

2-(2,4-Dichlorophenyl)-3-(4-[2-pyridyl]piperazin-1-yl)-1-(1H-1,2,4-triazol-1-yl)propan-2-ol The title compound, m.p. 116°–8°, was prepared similarly to the procedure of Example 4 starting from the same oxirane and 1-(2-pyridyl)piperazine. In this Example, the reaction mixture was however heated under reflux for 7 days and the eluent used in the flash chromatography stage was ethyl acetate:ether (1:1).

Analysis %: Found: C, 55.16; H, 5.08; N, 19.45; Calculated for $C_{20}H_{22}Cl_2N_6O$: C, 55.43; H, 5.12; N, 19.39.

EXAMPLE 7

(Alternative procedure to Example 4)

2-(2,4-Dichlorophenyl)-3-{4-(4-[1,1-dioxotetrahydrothiazin-4-yl]phenyl)piperazin-1-yl}-1-(1H-1,2,4-triazol-1-yl)propan-2-ol

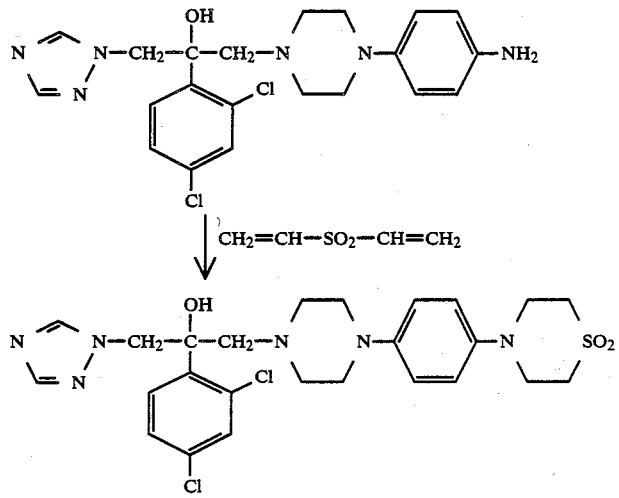

A mixture of 3-(4-[4-aminophenyl]-piperazin-1-yl)-2-(2,4-dichlorophenyl)-1-(1H-1,2,4-triazol-1-yl)propan-2-ol (0.6 g, 1.3 mmole) and divinylsulphone (1.17 g, 10 mmole) in ethanol (20 ml) was heated at reflux for 3 hours. After cooling, the solvent was removed under reduced pressure and the residue was partitioned between methylene chloride and water. The organic phase was separated, washed with water and dried over magnesium sulphate. After evaporation under reduced pressure, the product was purified by flash chromatography on silica gel eluting with ethyl acetate (95): diethylamine (5). The resulting product was re-chromatographed eluting with ethyl acetate (98.5): methanol (1.5) to yield, after collection and evaporation of appropriate fractions, the desired product as a foam, m.p. 69°–72° (0.41 g, 70%).

The compound was confirmed spectroscopically to be identical to the product of Example 4.

EXAMPLE 8

2-(2,4-Dichlorophenyl)-3-{cis-2,5-dimethyl-4-(4-[1,1-dioxotetrahydrothiazin-4-yl]phenyl)piperazin-1-yl}-1-(1H-1,2,4-triazol-1-yl)propan-2-ol (two diastereomers)

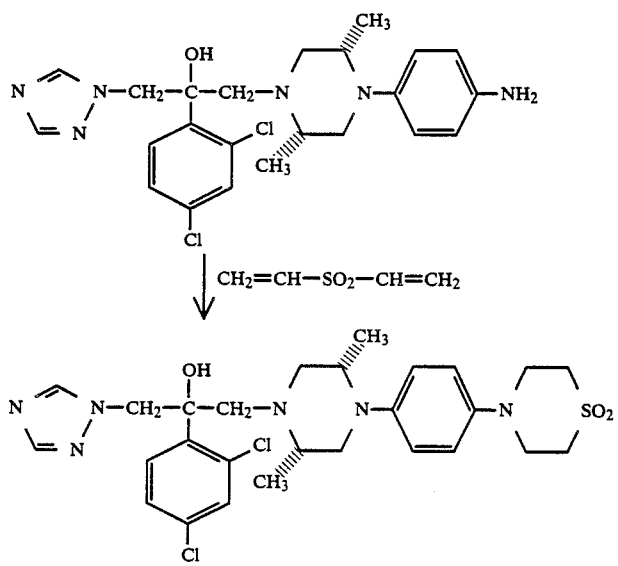

Diastereomer I

Diastereomer "I" of the title compound, m.p. 77°-80°, was prepared similarly to Example 7 using the appropriate aminophenyl-piperazine (diastereomer I, see Preparation 3) and divinylsulphone. Purification was carried out by flash column chromatography on silica gel eluting with methylene chloride:methanol:0.88 aqueous ammonia (98.5:1.5:0.2).

Analysis %: Found: C, 50.82; H, 5.50; N, 12.33; Calculated for $C_{27}H_{34}Cl_2N_6O_3S.\frac{3}{4} CH_2Cl_2$: C, 50.70; H, 5.41; N, 12.79.

Diastereomer II

This compound, m.p. 84°-5°, was prepared similarly to the procedure for diastereomer I but using, of course, diastereomer II of the piperazine starting material (see Preparation 3) and divinylsulphone.

Analysis %: Found: C, 52.68; H, 5.75; N, 14.35; Calculated for $C_{27}H_{34}Cl_2N_6O_3S.H_2O$: C, 53.02; H, 5.89; N, 13.75.

EXAMPLE 9

2-(2,4-Dichlorophenyl)-3-(4-[4-morpholinophenyl]piperazin-1-yl)-1-(1H-1,2,4-triazol-1-yl)propan-2-ol

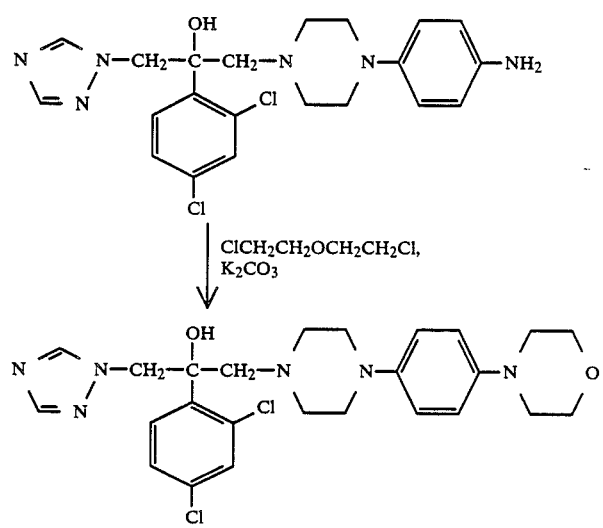

A mixture of 3-(4-[4-aminophenyl]-piperazin-1-yl)-2-(2,4-dichlorophenyl)-1-(1H-1,2,4-triazol-1-yl)propan-2-ol (400 mg, 0.9 mmole), bis-(2-chloroethyl)ether (244 mg, 1.7 mmole) and potassium carbonate (276 mg, 2 mmole) in ethanol (10 ml) was refluxed for 3 days. Following this, additional bis-(2-chloroethyl)ether (488 mg, 3.4 mmole) was added and heating was continued for a further 8 days. The solvent was then removed under reduced pressure and the residue partitioned between water and methylene chloride. The organic phase was separated, washed with water, dried over magnesium sulphate and purified by flash chromatogaraphy on silica gel eluting with ethyl acetate (96%): diethylamine (4%) to yield, after collection and evaporation of appropriate fractions, the title compound as a foam, m.p. 49°–50° after trituration with methylene chloride/hexane (0.21 g, 45%).

Analysis %: Found: C, 57.43; H, 5.95; N, 15.53; Calculated for $C_{25}H_{30}Cl_2N_6O_2.0.1\ CH_2Cl_2$: C, 57.31; H, 5.75; N, 15.99.

EXAMPLE 10

N-[4-(4-{2-[2,4-Dichlorophenyl]-2-hydroxy-1-[1H-1,2,4-triazol-1-yl]prop-3-yl}piperazin-1-yl)phenyl]-N',N'-dimethylformamidine

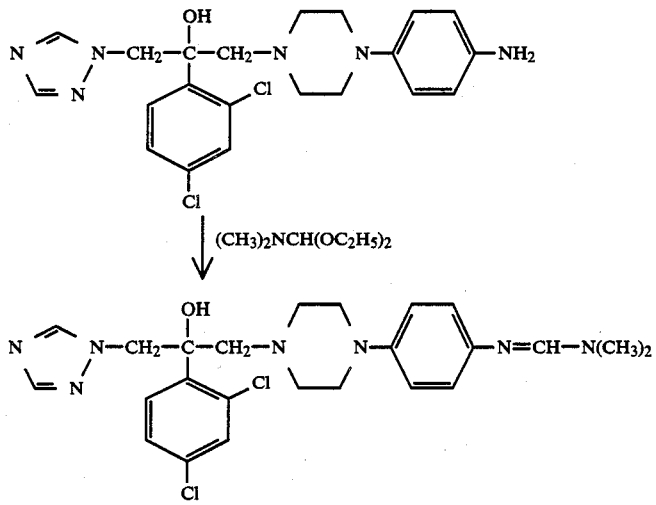

A mixture of 3-(4-[4-aminophenyl]-piperazin-1-yl)-2-(2,4-dichlorophenyl)-1-(1H-1,2,4-triazol-1-yl)propan-2-ol (160 mg, 0.36 mmole) and dimethylformamide diethyl acetal (70 mg, 0.47 mmole) was heated under reflux in ethanol (5 ml) for 14 hours. The solvent was then removed under reduced pressure and the residue was purified by flash chromatography on silica gel eluting with methylene chloride:methanol:0.88 ammonia solution (96:4:0.5) to yield, after collection and evaporation of appropriate fractions, the title compound as an amorphous solid, m.p. 63°–64° (0.153 g, 84%).

Analysis %: Found: C, 56.93; H, 5.79; N, 19.11; Calculated for $C_{24}H_{29}Cl_2N_7O$: C, 57.37; H, 5.78; N, 19.52.

The following Preparations, in which all temperatures are in °C., illustrate the preparation of the novel starting materials used in the previous Examples:

Preparation 1

1-[4-(1,1-Dioxotetrahydrothiazin-4-yl)phenyl]piperazine

(i) 4-Acetyl-1-(4-aminophenyl)piperazine

A suspension of 4-acetyl-1-(4-nitrophenyl)piperazine [C. A., 67, P101031Z] (30 g, 0.12 mole) and Raney nickel (2.5 g) in ethanol (500 ml) was hydrogenated at 60 psi (414 kPa) and 40° for 6 hours followed by 18 hours at room temperature. The catalyst was subsequently removed by filtration, the solvent removed under reduced pressure and the residue crystallized from ethyl acetate to yield the title compound, m.p. 129°–130° (18.4 g, 71%), which was used directly in the next stage.

(ii) 4-Acetyl-1-[4-(1,1-dioxotetrahydrothiazin-4-yl)phenyl]piperazine

A mixture of the product of part (i) (2.19 g, 10 mmole) and divinylsulphone (2.34 g, 19 mmole) in ethanol (20 ml) was heated under reflux for 4 hours followed by stirring overnight at room temperature. The resulting solid was collected by filtration, washed with ethanol and dried in vacuo to yield the title compound, (2.77 g, 82%), m.p. 196°–197°.

Analysis %: Found: C, 57.13; H, 6.92; N, 12.47; Calculated for $C_{16}H_{23}N_3O_3S$: C, 56.97; H, 6.83; N, 12.46.

(iii) 1-[4-(1,1-Dioxotetrahydrothiazin-4-yl)phenyl]piperazine hemihydrate

A mixture of the product of part (ii) (1.3 g, 3.8 mmole) and 5N hydrochloric acid (15 ml) was heated under reflux for 2 hous. The resulting mixture was con-

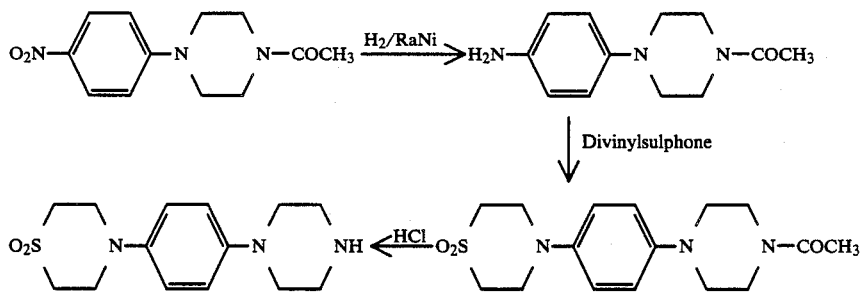

centrated under reduced pressure, the residue diluted with water (10 ml), neutralised with aqueous sodium bicarbonate and extracted into methylene chloride. After drying over magnesium sulphate, the organic phase was concentrated under reduced pressure to yield the title compound as a white solid, (0.6 g, 53%), m.p. 172°–173°.

Analysis %: Found: C, 55.55; H, 7.16; N, 13.77; Calculated for $C_{14}H_{21}N_3O_2S.\frac{1}{2}H_2O$: C, 55.27; H, 7.24; N, 13.82.

Preparation 2

3-(4-[4-Aminophenyl]-piperazin-1-yl)-2-(2,4-dichlorophenyl)-1-(1H-1,2,4-triazol-1-yl)propan-2-ol Analysis %: Found: C, 52.90; H, 4.96; N, 16.68; Calculated for $C_{21}H_{22}Cl_2N_6O_3.\frac{5}{8} CH_3COOC_2H_5$: C, 52.93; H, 4.87; N, 16.59.

(ii)
3-(4-[4-Aminophenyl]piperazin-1-yl)-2-(2,4-dichlorophenyl)-1-(1H-1,2,4-triazol-1-yl)propan-2-ol To a solution of the product of part (i) (0.55 g, 1.15 mmole) in acetic acid (20 ml) was added 10% palladium-on-charcoal (50 mg) and the mixture was hydrogenated at 15 psi (103 kPa) for 4 hours. The catalyst was then removed by filtration, the solvent removed under reduced pressure, and the residue partitioned between methylene chloride and water. The organic phase was

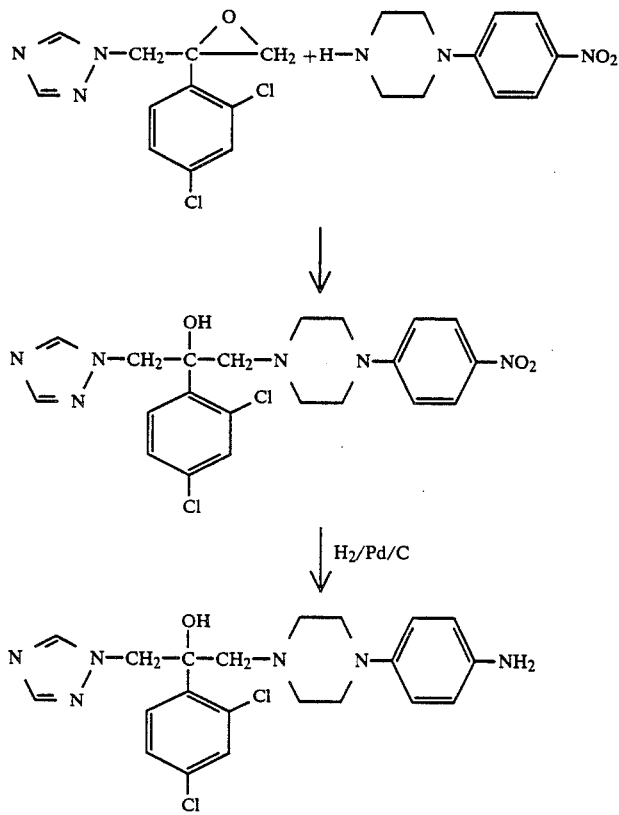

(i)
2-(2,4-Dichlorophenyl)-3-(4-[4-nitrophenyl]piperazin-1-yl)-1-(1H-1,2,4-triazol-1-yl)propan-2-ol The title compound, m.p. 168°, was prepared similarly to Example 4 starting from the appropriate piperazine and oxirane. In the flash chromatography stage, the eluent was ethyl acetate. The product was crystallized from ethyl acetate/hexane.

separated, washed again with water, dried over magnesium sulphate and concentrated under reduced pressure to yield the title compound as a foam, m.p. 60° (0.485 g, 94%).

Analysis %: Found: C, 55.69; H, 5.45; N, 18.19. Calculated for $C_{21}H_{24}Cl_2N_6O.\frac{1}{2}H_2O$: C, 55.26; H, 5.48; N, 18.42.

Preparation 3

3-(4-[4-Aminophenyl]-cis-2,5-dimethylpiperazin-1-yl)-2-(2,4-dichlorophenyl)-1-(1H-1,2,4-triazol-1-yl)propan-2-ol (separated diastereomers)

(ii) 2,4-Dichlorophenyl-3-(4-[4-nitrophenyl-cis-2,5-dimethylpiperazin-1-yl)-1-(1H-1,2,4-triazol-1-yl)propan-2-ol (two diastereomers)

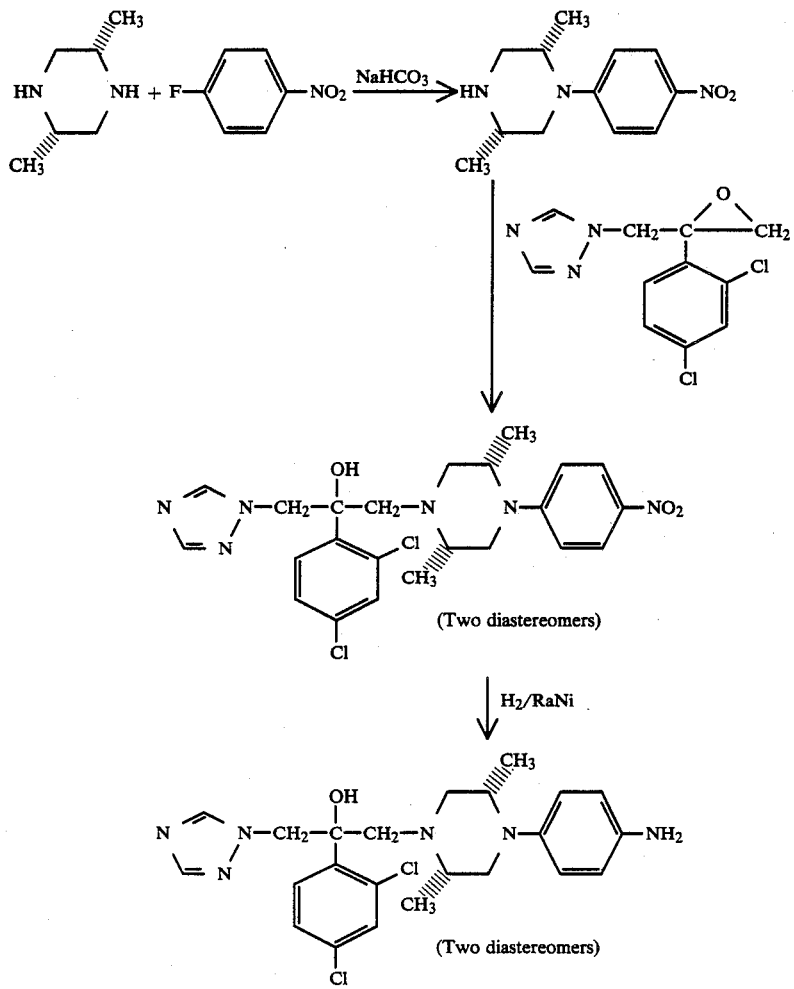

(i) 4-Nitrophenyl-cis-2,5-dimethylpiperazine

A mixture of 4-fluoronitrobenzene (30.34 g, 0.22 mole), cis-2,5-dimethylpiperazine (25 g, 0.22 mole) and sodium bicarbonate (24 g, 0.28 mole) in n-pentanol (150 ml) was heated under nitrogen at 90°–100° for 18 hours. After filtration, the n-pentanol was removed under reduced pressure and the residue was partitioned between methylene chloride and water. The organic phase was separated, washed again with water, dried over magnesium sulphate, and concentrated under reduced pressure. The residue was triturated with ice water to yield a yellow solid. The solid was filtered off and dried to yield the title compound, m.p. 93°–4° (37 g, 71%).

Analysis %: Found: C, 60.63; H, 7.31; N, 17.66; Calculated for $C_{12}H_{17}N_3O_2.0.1\ H_2O$: C, 60.81; H, 7.26; N, 17.74.

A mixture of the product of part (i) (2.7 g, 11 mmole) and 2-(2,4-dichlorophenyl)-2-(1H-1,2,4-triazol-1-ylmethyl) oxirane (2.7 g, 10 mmole) in n-pentanol (30 ml) was heated under reflux for 48 hours. The solvent was then removed under reduced pressure and the residue suspended in hot ethyl acetate. After cooling, the insoluble material was removed by filtration to yield diastereomer I of the title compound (1.1 g, 22%), m.p. 212°.

Analysis %: Found: C, 54.48; H, 5.32; N, 16.38; Calculated for $C_{23}H_{26}Cl_2N_6O_3$: C, 54.65; H, 5.15; N, 16.63.

The filtrate was concentrated under reduced pressure and chromatographed on silica gel eluting with ethyl acetate (70%): hexane (25%): diethylamine (5%) to yield, firstly, after collection and evaporation of appropriate fractions, an additional batch of diastereomer I (0.22 g, 4%), and, secondly, diastereomer II (0.9 g, 18%). Diastereomer II had an m.p. of 181°–2° and the following analysis:

Analysis %: Found: C, 55.08; H, 5.28; N, 15.81; Calculated for $C_{23}H_{26}Cl_2N_6O_3.\frac{1}{4}\ CH_3CO_2Et$: C, 54.65; H, 5.31; N, 15.94.

(iii)

3-(4-[4-Aminophenyl]-cis-2,5-dimethylpiperazin-1-yl)-2-(2,4-dichlorophenyl)-1-(1H-1,2,4-triazol-1-yl)propan-2-ol (two diastereomers)

The separated diastereomers I and II from step (ii) were each reduced with H₂/Pd/C similarly to Preparation 2(ii) to yield the two diastereomers of the title compound.

Diastereomer I, m.p. 74°–5°.

Analysis %: Found: C, 57.90; H, 5.76; N, 17.33; Calculated for $C_{23}H_{28}Cl_2N_6O$: C, 58.11; H, 5.90; N, 17.68.

Diastereomer II, m.p. 58°–9°.

Analysis %: Found: C, 55.43; H, 5.76; N, 16.06; Calculated for $C_{23}H_{28}Cl_2N_6O \cdot 0.4\ CH_2Cl_2$: C, 55.16; H, 5.65; N, 16.50.

Preparation 4

1-(Benzoxazol-2-yl)piperazine

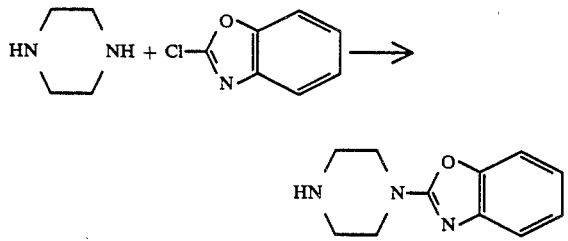

To a stirred solution of piperazine (8 g, 93 mmole) in ethanol (30 ml) was added 2-chlorobenzoxazole (3 g, 19.5 mmole) dropwise. The resulting reaction was exothermic. The mixture was then stirred for 18 hours at room temperature, quenched by the addition of methylene chloride (50 ml) and the resulting precipitate removed by filtration. The filtrate was concentrated under reduced pressure then purified by flash column chromatography on silica gel eluting with methylene chloride:methanol: 0.88 ammonia solution (90:10:1) to yield the title compound, m.p. 70°–72° (1.8 g, 46%), which was used directly.

We claim:

1. A compound of the formula:

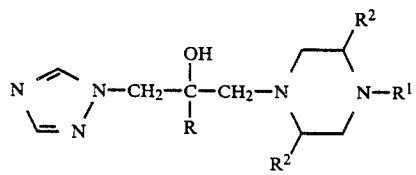

where

R is a phenyl or halo substituted phenyl;

R¹ is substituted phenyl wherein the substituent is —N=CH—N(C₁–C₄ alkyl)₂,

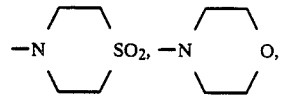

pyridyl, benzothiazolyl, benzoxazolyl or quinolyl; and

R² is H or CH₃; or a C₂–C₄ alkanoyl or benzoyl ester or a pharmaceutically acceptable salt thereof.

2. A compound as claimed in claim 1, wherein the phenyl substituent is 2,4-pyridyl, 2-quinolyl, 2-benzothiazolyl or 2-benzoxazolyl.

3. A compound as claimed in claim 2, wherein R is 2,4-dichlorophenyl or 2,4-difluorophenyl.

4. The compound as claimed in claim 3 wherein R is 2,4-dichlorophenyl; R² is H; and R¹ is 2-pyridylphenyl.

5. A compound as claimed in claim 1, wherein R¹ is substituted phenyl wherein the substituent is

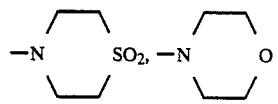

or —N=CH—N(C₁–₄ alkyl)₂.

6. A compound as claimed in claim 5 wherein R¹ is

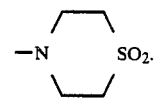

7. The compound as claimed in claim 6 wherein R is 2,4-difluorophenyl and R² is H.

8. The compound as claimed in claim 6 wherein R is 2,4-dichlorophenyl and R² is H.

9. The compound as claimed in claim 6 wherein R is 2,4-dichlorophenyl and R² is CH₃.

10. A composition comprising a compound as claimed in claim 1 and a pharmaceutically or agriculturally carrier.

11. A method for treating fungal infections in a host suffering therefrom which comprises administering to said host an antifungally effective amount of a compound as claimed in claim 1.

12. A compound of the formula:

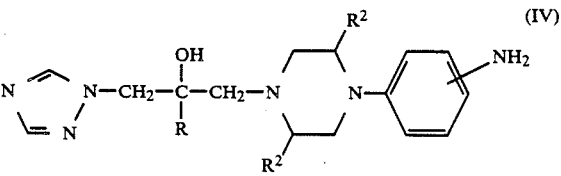

wherein R is phenyl or halo substituted phenyl; R² is H or CH₃; and R¹ is substituted phenyl wherein the substituent is —N=CH—N(C₁–₄ alkyl)₂,

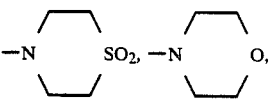

pyridyl, benzothiazolyl, benzoxazolyl or quinolyl.

* * * * *